US007667009B2

(12) United States Patent
Koyanagi et al.

(10) Patent No.: US 7,667,009 B2
(45) Date of Patent: Feb. 23, 2010

(54) METHOD FOR PURIFYING MODIFIED MAJOR MITE ALLERGEN

(75) Inventors: Satoshi Koyanagi, Kikuchi (JP); Kenjiro Kawatsu, Kikuchi (JP); Toshio Murakami, Kikuchi (JP); Yoshinobu Miyatsu, Kikuchi (JP); Toshihiro Maeda, Kikuchi (JP); Hiroshi Mizokami, Kikuchi (JP)

(73) Assignee: Juridical Foundation the Chemo-Sero-Therapeutic Research Institute, Kumamoto-ken (JO)

( * ) Notice: Subject to any disclaimer, the term of this patent is extended or adjusted under 35 U.S.C. 154(b) by 506 days.

(21) Appl. No.: 10/555,883

(22) PCT Filed: Apr. 14, 2004

(86) PCT No.: PCT/JP2004/005315

§ 371 (c)(1),
(2), (4) Date: Nov. 7, 2005

(87) PCT Pub. No.: WO2004/099406

PCT Pub. Date: Nov. 18, 2004

(65) Prior Publication Data

US 2008/0113424 A1 May 15, 2008

(30) Foreign Application Priority Data

May 7, 2003 (JP) ............................ 2003-128610

(51) Int. Cl.
*A23J 1/00* (2006.01)

(52) U.S. Cl. ....................... 530/412; 530/414; 530/416; 530/417

(58) Field of Classification Search ....................... None
See application file for complete search history.

(56) References Cited

U.S. PATENT DOCUMENTS

| | | | | |
|---|---|---|---|---|
| 5,912,327 | A * | 6/1999 | Li et al. | 530/412 |
| 6,632,425 | B1 * | 10/2003 | Li et al. | 424/85.1 |
| 2002/0054881 | A1 | 5/2002 | Sturaro et al. | |
| 2004/0024186 | A1 * | 2/2004 | Li et al. | 530/351 |

FOREIGN PATENT DOCUMENTS

| | | |
|---|---|---|
| EP | 0 819 763 A1 | 1/1998 |
| JP | 6-253851 | 9/1994 |
| JP | 2001-231562 | 8/2001 |
| JP | 2001-231563 | 8/2001 |
| WO | WO 96/30539 A1 | 10/1996 |

OTHER PUBLICATIONS

Mukhopadhyay et al. 'Inclusion bodies and purfication of proteins in biologically active forms.' Adv. Biochem. Eng. 56:61-109, 1997.*

Thomas A.E. Platts-Mills et al; "Dust mites: Immunology, allergic disease, and environmental control"; *The Journal of Allergy and Clinical Immunology*; vol. 80, pp. 755-775, 1987.

Toshifumi Yuuki et al; "Cloning and Sequencing of cDNAs corresponding to mite major allergen"; *Japanese J. Allergology*, vol. 39, pp. 557-561, 1990.

"Shin Seikagaku Jikken Koza 1 Tanpakushitsu I-Bunri Seisei Seishitsu" (New Lecture on Biochemical Experiment 1: Isolation, Purification and Property), edited by The Japanese Biochemical Society, published on Feb. 26, 1990, pp. 169-177 and 184-194.

"Tanpakushitsu Kogaku" (Protein Engineering), edited by Kin'ichiro Miura et al, published on Jul. 16, 1988, p. 118.

Toshiro Takai et al; "Engineering of the Major House Dust Mite Allergen DER f 2 for Allergen-Specific Immunotherapy"; Nature Biotechnology; Aug. 15, 1997; pp. 754-758 ISSN: 1087-0156; vol. 15; Publishing Group, New York, NY US.

* cited by examiner

*Primary Examiner*—Maher M Haddad
*Assistant Examiner*—Nora M Rooney
(74) *Attorney, Agent, or Firm*—Browdy and Neimark, PLLC

(57) ABSTRACT

A method for purifying a modified major mite allergen obtained by the genetic recombination technique and a purified modified major mite allergen obtained by said method for purification are provided. A method for purifying a modified major mite allergen obtained by the genetic recombination technique, which comprises the purification steps: (1) Washing and recovering inclusion bodies containing a modified major mite allergen obtained by the genetic recombination technique with MF membrane; (2) Dissolving said inclusion bodies followed by refolding; (3) Concentrating a solution containing the modified major mite allergen with simultaneous removal of low molecular weight components with ultrafiltration membrane; (4) Recovering the modified major mite allergen in non-adsorbed fractions with an anion exchanger; (5) Recovering the modified major mite allergen in adsorbed fractions with a hydrophobic gel; and (6) Recovering the modified major mite allergen in adsorbed fractions with an anion exchanger, and a modified major mite allergen with high purity obtained by said method for purification.

2 Claims, 10 Drawing Sheets

SEQUENCE LISTING

```
<160> NUMBER OF SEQ ID NOS: 2

<210> SEQ ID NO 1
<211> LENGTH: 30
<212> TYPE: DNA
<213> ORGANISM: Artificial Sequence
<220> FEATURE:
<223> OTHER INFORMATION: PCR primer

<400> SEQUENCE: 1
```

-continued

```
cggttcgaat ggatcaagtc gatgttaaag                                   30


<210> SEQ ID NO 2
<211> LENGTH: 30
<212> TYPE: DNA
<213> ORGANISM: Artificial Sequence
<220> FEATURE:
<223> OTHER INFORMATION: PCR primer

<400> SEQUENCE: 2

gcttcgcgat cattaatcac ggattttagc                                   30
```

METHOD FOR PURIFYING MODIFIED MAJOR MITE ALLERGEN

TECHNICAL FIELD

The present invention relates to a method for purifying a modified major mite allergen obtained by the genetic recombination technique using *E. coli* as a host. More specifically, the present invention relates to a method for purifying a modified major mite allergen comprising steps: (1) washing and recovering inclusion bodies containing a modified major mite allergen with MF membrane; (2) dissolving/refolding of said inclusion bodies; (3) treatment with ultrafiltration membrane; (4) treatment with an anion exchanger to recover non-adsorbed fractions; (5) treatment with a hydrophobic gel to recover adsorbed fractions; and (6) treatment with an anion exchanger to recover adsorbed fractions, and a highly purified modified major allergen obtained by said method for purification.

BACKGROUND ART

For therapy of allergic diseases such as allergic asthma, allergic rhinitis, allergic dermatitis and allergic conjunctivitis, an anti-allergic or anti-histaminic agent is used in general. This therapy, however, being a symptomatic treatment, is unable to radically cure allergic diseases. Hyposensitization where causative antigens of allergic diseases are injected is believed to be a sole measure for radical cure of allergic diseases. Hyposensitization is performed by injecting to a patient suffering from allergic diseases a small amount of allergens causative for said allergic diseases so that allergic reactions within the living body might disappear. Its efficacy is more than 70%.

Sole mite allergen preparations currently used are house dust allergen preparations, which are prepared by the process of extracting allergens from house dust. The mite allergen preparations prepared by said process thus also contain a variety of antigens such as e.g. mould or bacteria in addition to mite thereby not to allow for unambiguously defining their biological activity (titer). There is also a problem that stable provision of a large quantity of allergens is difficult due to a limited source material therefor.

Allergen preparations are mainly administered subcutaneously for immune induction. If allergen preparations are contaminated with impurities, however, the living body receiving said preparations will possibly induce an immune response to the undesired impurities to thereby establish sensitization thereto. Thus, there is possibility that allergy to impurities is newly induced to cause serious adverse side effects. Accordingly, to ensure that allergen preparations are safe, highly purified preparations need be provided.

However, even if allergen preparations are highly purified, there is still a risk that administering the preparations causes anaphylactic shock. It is known that type I allergy, typically anaphylactic shock, is caused when allergens bind IgE antibody and hence administration of allergens always involves some risk of causing anaphylactic shock.

In recent years, with progress of study in mite allergens, several major mite allergens have already been identified (e.g. Platts-Mills et al., J. Allergy Clin. Immunol. 80, 755-775, 1987; incorporated herein by reference). For instance, Yuhki et al. disclosed a gene encoding major mite allergen Der f 2 and a process for preparing the same (Japanese J. Allergology, vol. 39, p. 557, 1990; incorporated herein by reference). Hyposensitization for therapy of allergic diseases using this major mite allergen might be quite efficacious solving the problems as described above but is not able to completely exclude risk of anaphylactic shock possibly caused by administration of allergens.

A modified type of a major mite allergen (hereinafter also referred to as "modified major mite allergen") has been prepared using the genetic recombination technique wherein a steric structure of mite allergen is partly destructed so as to reduce its binding to IgE antibody (e.g. Japanese Patent Publication No. 253851/1994 (Japanese Patent Application No. 139793/1993); incorporated herein by reference). This modified major mite allergen, resulting from replacement of the cysteine residue in major mite allergen Der f 2 with the serine residue, is expected to be useful as a medicament for therapy of allergy by safely inducing hyposensitization without causing anaphylactic shock. However, there is no report that major mite allergens produced by the genetic engineering process on an industrial level are purified to a pharmaceutical grade.

A recombinant major mite allergen Der f 2 has been prepared by transforming prokaryotes or eukaryotes with an expression vector comprising a gene encoding Der f 2, culturing the transformants and purifying Der f 2 from the culture. According to the process disclosed in Japanese Patent Publication No. 253851/1994 as described above, purification from culture is performed by ion exchange chromatography and gel filtration chromatography. However, the thus purified Der f 2 has purity of merely a reagent grade. Moreover, according to the process, refolding of the modified mite allergen is performed by dialysis and hence treatment in a large quantity is difficult.

DISCLOSURE OF THE INVENTION

Technical Problem to be Solved by the Invention

An object of the present invention is to provide a method for purifying a modified major mite allergen produced by the genetic engineering process to a pharmaceutical grade.

Another object of the present invention is to provide a modified major mite allergen of high purity that is obtained by the method for purification of the present invention and does not comprise contaminants such as host-derived components.

Means for Solving the Problems

In order to attain the objects described above, the present inventors have carried out intensive investigation and as a consequence found that a modified major mite allergen may efficiently be purified from culture of host cells producing the modified major mite allergen by the steps: (1) washing and recovering inclusion bodies containing a modified major mite allergen obtained by the genetic engineering process with MF membrane; (2) dissolving said inclusion bodies followed by refolding; (3) concentrating a solution containing the modified major mite allergen with simultaneous removal of low molecular weight components with ultrafiltration membrane; (4) recovering the modified major mite allergen in non-adsorbed fractions with a weak anion exchanger; (5) recovering the modified major mite allergen in adsorbed fractions with a hydrophobic gel; and (6) recovering the modified major mite allergen in adsorbed fractions with a strong anion exchanger, to thereby complete the present invention.

Thus, the present invention relates to a method for purifying a modified major mite allergen obtained by the genetic recombination technique, which comprises the purification steps:

(1) Washing and recovering inclusion bodies containing a modified major mite allergen obtained by the genetic recombination technique with MF membrane;

(2) Dissolving said inclusion bodies followed by refolding;

(3) Concentrating a solution containing the modified major mite allergen with simultaneous removal of low molecular weight components with ultrafiltration membrane;

(4) Recovering the modified major mite allergen in non-adsorbed fractions with an anion exchanger;

(5) Recovering the modified major mite allergen in adsorbed fractions with a hydrophobic gel; and (6) Recovering the modified major mite allergen in adsorbed fractions with an anion exchanger.

Specifically, the present invention provides the method for purification as described above, which comprises the purification steps:

(1) With deionized water and MF membrane, washing and recovering inclusion bodies containing a modified major mite allergen by repeating the procedures of dilution and concentration of debris of *E. coli* producing the modified major mite allergen that had been cultured and induced for expression;

(2) Dissolving said inclusion bodies in a solution containing a reducing agent and a denaturing agent and then diluting or removing said denaturing agent for refolding;

(3) With ultrafiltration membrane of fractionation M. W. of 6,000 to 10,000, concentrating a solution containing the modified major mite allergen and removing low molecular weight components;

(4) With a weak anion exchanger column, recovering the modified major mite allergen in non-adsorbed fractions under conditions of pH 8 to 9 and a salt concentration of 0.03 to 0.1M;

(5) With a hydrophobic column, recovering the modified major mite allergen in adsorbed fractions by first letting the modified major mite allergen adsorbed at pH 7 to 8 and at 2 to 3M sodium chloride and then eluting the modified major mite allergen at a salt concentration of 0 to 1M; and (6) With a strong anion exchanger column, recovering the modified major mite allergen in adsorbed fractions by first letting the modified major mite allergen adsorbed at pH 8.5 to 9.5 and at 1 to 3M urea and then eluting the modified major mite allergen through linear alteration of a salt concentration from 0 to 0.1M.

The present invention further relates to a purified modified major mite allergen obtained in accordance with the method for purification as described above.

Specifically, in case that a modified major mite allergen obtained by the genetic recombination technique is a modified major mite allergen Der f 2 wherein both the cysteine residues at 8-position and 119-position in Der f 2 are replaced with serine residues, the present invention relates to the modified major mite allergen Der f 2 obtained by the method for purification as described above as well as a composition comprising said modified major mite allergen as a major component, said modified major mite allergen Der f 2 having a molecular weight of about 15 kD and isoelectric point of pI 6.6 to 7.2 and being characterized by the following properties:

(1) It exhibits a single band in SDS-PAGE analysis;

(2) It has a content of contaminating proteins from a host that is 1% or less;

(3) It has a content of a polymer of the modified major mite allergen that is 10% or less;

(4) It has a content of the modified major mite allergen with distinct steric structure that is 10% or less; and (5) An endotoxin content of a solution containing 500 μg/ml of the modified major mite allergen is 0.25 EU/ml or less; and more specifically being characterized by the following properties:

(1) It exhibits a single band in SDS-PAGE analysis;

(2) It has a content of contaminating proteins from a host that is 0.004 to 1%;

(3) It has a content of a polymer of the modified major mite allergen that is 0.005 to 10%;

(4) It has a content of the modified major mite allergen with distinct steric structure that is 0.03 to 10%; and (5) An endotoxin content of a solution containing 500 μg/ml of the modified major mite allergen is from 0.002 to 0.25 EU/ml.

MORE EFFICACIOUS EFFECTS THAN PRIOR ART

In accordance with the method of the present invention, a modified major mite allergen obtained by the genetic engineering process may be purified efficiently and in a large quantity. Thus, the method of the present invention is suitable for industrial production of the modified major mite allergen and allows for stably providing allergen preparations containing a single modified major mite allergen. Moreover, by performing the purification process with a strong anion exchanger column in the presence of urea, purity of the desired modified major mite allergen may effectively be increased.

In particular, in case that a modified major mite allergen obtained by the genetic recombination technique is a modified major mite allergen Der f 2 wherein both the cysteine residues at 8-position and 119-position in Der f 2 are replaced with serine residues, said modified major mite allergen Der f 2 having reduced binding to IgE antibody due to partial destruction of its steric structure unlike native major mite allergens, purification of said modified major mite allergen by the method in accordance with the present invention allows for provision of modified major mite allergen preparations with reduced risk of causing anaphylactic shock. In accordance with the method of the present invention, a modified major mite allergen of high purity may be provided that has the following properties: (1) a single band in SDS-PAGE analysis; (2) a content of contaminating proteins from a host that is 0.1% or less; (3) a content of a polymer of the modified major mite allergen that is less than a detection limit; (4) a content of the modified major mite allergen with distinct steric structure that is 10% or less; and (5) an endotoxin content of a solution containing 500 μg/ml of the modified major mite allergen that is less than 0.25 EU/ml, a quality standard for water for injection (Japanese Pharmacopoeia, 14th edition). Thus, in accordance with the method of the present invention, host-derived contaminants may substantially be excluded so as to obviate serious adverse side effects due to said contaminants and hence safe modified major mite allergen preparations may be provided.

BEST MODE FOR CARRYING OUT THE INVENTION

Figure 1:
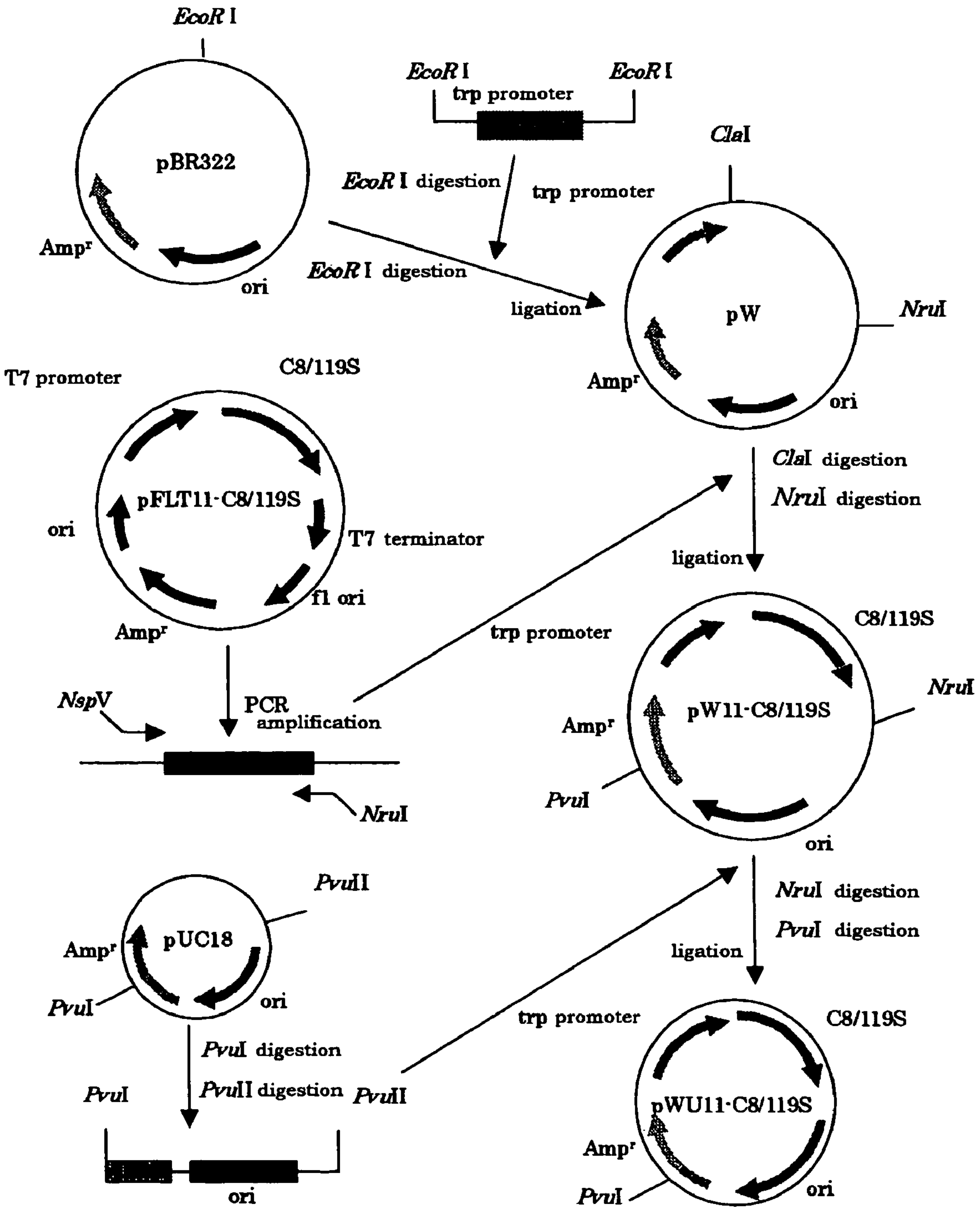
FIG. 1 shows construction of an expression vector pWU11-C8/119S.

The method for purification of the present invention comprises the steps: (1) washing and recovering inclusion bodies containing a modified major mite allergen obtained by the genetic engineering process with MF membrane; (2) dissolving said inclusion bodies followed by refolding; (3) concentrating a solution containing the modified major mite allergen with simultaneous removal of low molecular weight components with ultrafiltration membrane; (4) recovering the modified major mite allergen in non-adsorbed fractions with an anion exchanger; (5) recovering the modified major mite allergen in adsorbed fractions with a hydrophobic gel; and (6) recovering the modified major mite allergen in adsorbed fractions with an anion exchanger.

Each of the steps comprised of the method is explained in detail below.

Preparation of a Culture Containing a Modified Major Mite Allergen by the Genetic Recombination Technique A modified major mite allergen obtained by the genetic recombination technique to be purified by the method for purification according to the present invention may include those prepared by using the major mite allergen genes identified hitherto such as Der f 2 and Der p 2. The major mite allergens Der f 2 and Der p 2 share homology of 80% or more at an overall amino acid sequence level (Chua K.Y., Int. Arch. Allergy Appl. Immunol. 91(2), 118-123 (1990)) and have the S—S bond at the identical position. Thus, a modified major mite allergen of interest may be obtained from a nucleic acid fragment containing any of these major mite allergen genes by partially altering their nucleotide sequences.

By way of example, a modified major mite allergen that may be used in the method of the present invention includes for instance a modified major mite allergen Der f 2 wherein both the cysteine residues at 8-position and 119-position in Der f 2 are replaced with serine residues as described in Japanese Patent Publication No. 253851/1994. In addition to this, any other modified major mite allergens may be used wherein their binding to IgE is reduced through modification of their steric structure.

A major mite allergen gene as well as a modified major mite allergen gene wherein replacement is made in a portion of its nucleotide sequence may be prepared using as a starting material mRNAs or genomic DNAs extracted from mites in accordance with the common genetic recombination technique as described by Sambrook (Molecular Cloning, A Laboratory Manual Second Ed., Cold Spring Harbor Laboratory Press, N.Y., 1989).

In practice, commercially available kits may be used. For instance, for extraction of RNAs, reagents such as TRIzol reagent (Invitrogen), ISOGEN (NIPPON GENE CO., LTD.), and StrataPrep Total RNA Purification Kit (TOYOBO) may be used; for purification of mRNAs, kits such as mRNA Purification Kit (Amersham Bioscience), Poly(A) Quick mRNA Isolation Kit (TOYOBO), and mRNA Separator Kit (Clontech) may be used; for conversion into cDNAs, SuperScript plasmid system for cDNA synthesis and plasmid cloning (Invitrogen), cDNA Synthesis Kit (TAKARA SHUZO CO., LTD.), SMART PCR cDNA Synthesis & Library Construction Kits (Clontech), Directionary cDNA Library Construction systems (Novagen Inc.) may be used.

Specifically, a modified major mite allergen gene may be obtained by preparing a plasmid bearing cDNA of a modified major mite allergen and performing PCR using said plasmid as a template in accordance with the method described in Japanese Patent Publication No. 253851/1994.

A modified major mite allergen may be produced by introducing the modified major mite allergen gene into a suitable host including, for instance, an animal cell, a plant cell, an insect cell and a microorganism such as *E. coli*, yeast and *Bacillus subtilis*. It may also be produced by various animals, so-called animal factory.

A material containing a modified major mite allergen for use in the present invention may be any material that is prepared by the genetic engineering process and include those known in the art as published in literatures and ones that will be developed in future, including, for instance, a culture of the host as described above producing a modified major mite allergen and a body fluid or secretion from various recombinant animals. Preferably, a culture of *E. coli* producing a modified major mite allergen may be used.

More preferably, a culture of *E. coli* producing a modified major mite allergen may be used wherein expression is induced without an inducer such as indoleacetic acid (IAA) or isopropyl-1-thio-β-D-galactopyranoside (IPTG). A culture containing a modified major mite allergen but not containing an inducer may be obtained for instance by the method as described in Japanese Patent Application No. 2003-58992.

Specifically, a modified major mite allergen gene is incorporated into an expression plasmid comprising a tryptophan promoter and a replication origin from pUC and *E. coli* is then transformed with the expression plasmid to prepare *E. coli* producing a modified major mite allergen and a glycerol stock thereof. Using the glycerol stock as a seed, two-step culture is performed. Firstly, culture is performed at low temperature (25 to 32° C.) so that the cells are sufficiently proliferated. Next, culture temperature is shifted to high temperature (37 to 38° C.) to allow for expression of a modified major mite allergen. Such a two-step culture will enable obtaining a culture containing a modified major mite allergen but not containing an inducer.

A term of culture may vary depending on a culture temperature and a scale of production of a major mite allergen. Culture at low temperature may be continued until the recombinant *E. coli* cells are proliferated to the median of a logarithmic growth phase. Culture at high temperature may be continued until an expression level of a major mite allergen reached its peak. For instance, 10 ml of the recombinant *E. coli* (pWU11-C8/119S/HB101) glycerol stock obtained in Example 1 is inoculated to about 1 L of culture medium. After culture at 32° C. for 6 to 10 hours, the cells are then inoculated to 200 to 300 L of culture medium for culture at 25° C. for 12 to 17 hours. Next, the cells are cultured at 37° C. for 8 to 16 hours to produce about 7 to 10 g/L of inclusion bodies as a wet weight containing a modified major mite allergen.

Purification of a Modified Major Mite Allergen (i) Recovery of Inclusion Bodies

A culture is initially concentrated with MF membrane (ASAHIKASEI) so as to recover cells. MF membrane as used herein may preferably have a size of 0.1 to 0.25 μm. Recovered cells are disrupted in an appropriate way to release inclusion bodies containing a modified major mite allergen out of the cells. Cells may be disrupted by any means such as lysing cells with e.g. a chemical substance, a surfactant or an enzyme or physical treatment with French Press or sonication. Any of these treatments may be combined together so that the cells are more efficiently disrupted. For instance, the cells recovered by MF membrane are diluted and concentrated with deionized water to remove the remaining culture components and metabolites from the cells and then added with an appropriate buffer and lysozyme. The mixture is left to stand at low temperature (4 to 15° C.) overnight to lyse the cell wall of the cells and subject to French Press (manufactured by GAULIN CORPORATION) at 500 to 600 kg/$cm^2$ to thereby disrupt the cells. A buffer as used herein may be any buffer that exerts a buffer capacity at a pH range where lysozyme may act (7.5 to 9) such as Tris buffer. A concentration of a buffer may be in such a range that a usual buffer is commonly used (10 to 50 mM). Lysozyme may be used at a concentration of 0.3 to 1.0 g/L. For instance, 20 mM Tris buffer at pH 8.5 and then lysozyme (0.6 g/L) are added to the cells and the mixture is left to stand at 4° C. overnight to lyse the cell wall. After the cells are disrupted with French Press, dilution and concentration of the resulting debris are repeated with deionized water and MF membrane to successfully remove most of the cellular components. Inclusion bodies may be recovered as a precipitate by centrifugation of a concentrate containing the inclusion bodies (ii) Refolding The recovered inclusion bodies are then dissolved in a solution containing a reducing agent and a denaturing agent. For a reducing agent as used herein, cysteine, glutathione, dithiothreitol and 2-mercaptoethanol may be used. Any of these reducing agents may also be used in combination. A reducing agent may be used at a concentration of 10 to 100 mM, preferably 10 to 50 mM, although it may vary depending on an amount of the inclusion bodies to be dissolved. For a denaturing agent, urea and guanidine hydrochloride may be used, preferably urea. Urea and guanidine hydrochloride may be used at a concentration of 4 to 8 M and 2 to 6 M, respectively. For use in the present invention, 8 M urea is preferable. When a denaturing agent and a reducing agent are dissolved, a buffer at pH 7 to 11, preferably pH 8 to 9, is used. A buffer as used herein may be any buffer that exerts a buffer capacity at the pH range as described above such as phosphate buffer, Tris buffer, glycine buffer, carbonate buffer and the like, preferably the one as described in (i) recovery of inclusion bodies above. Specifically, the inclusion bodies are dissolved in Tris buffer at pH 8.5 containing 20 mM cysteine and 8 M urea. A temperature at which the inclusion bodies are dissolved may be any temperature that is 40° C. or less. A dissolution time may be adjusted while observing a state of dissolution of the inclusion bodies and the mixture is typically stirred for 30 minutes to 1 hour.

Next, to a solution of the inclusion bodies are added 10- to 20-folds amount of a redox buffer based on the solution to allow for refolding, i.e. reformation of S—S bond under oxidative condition to form a normal steric structure. A reducing agent and an oxidizing agent as used herein include cysteine and cystine, respectively. Cysteine and cystine may be used in a concentration of 1 mM to 10 mM and 0.1 mM to 1 mM, respectively. Cystine may preferably be used at 1/10 amount relative to cysteine.

A type and a concentration of a buffer used for refolding may be the same as those used for dissolving the inclusion bodies. A buffer may be used at pH 7.5 to 9. Specifically, 20 mM Tris buffer at pH 8.5 containing 3 mM cysteine and 0.3 mM cystine is used for refolding by diluting or removing the denaturing agent. For removal of the denaturing agent, dialysis, gel filtration and the like are used. A temperature at which the refolding is performed may be any temperature that is room temperature or less. Refolding may be performed by letting the solution left to stand for 1 to 7 days, preferably for 3 to 4 days.

The refolding reaction may be quenched by adding an acidic buffer such as acetic acid or hydrochloric acid so as to adjust the pH of the reaction solution to neutrality. Specifically, the refolding reaction is quenched by titration of the reaction solution to pH 7 with 30% acetic acid.

(iii) Ultrafiltration

After treatment for refolding, the solution containing a modified major mite allergen is subject to treatment with ultrafiltration membrane of fractionation M. W. of 6,000 to 10,000 for concentration and removal of low molecular weight components. To the resultant concentrate is added sodium chloride at a final concentration of 30 to 100 mM and the mixture is adjusted to pH 8 to 9 with an alkaline solution. Precipitates formed may be removed with a filter of ϕ0.45 μm. Preferably, to the concentrate is added sodium chloride at a final concentration of 50 mM and the mixture is adjusted to pH 8.5 with 5N sodium hydroxide solution. The ultrafiltration treatment may be performed at room temperature or less. The obtained solution containing a modified major mite allergen is subject to the following purification process.

(iv) Recovery of Non-Adsorbed Fractions with Treatment with Anion Exchanger

After treatment with ultrafiltration, the solution containing a modified major mite allergen is passed through an anion exchanger column and effluent fractions are recovered as containing a modified major mite allergen. This process may be performed at 5 to 10° C. An example of an anion exchanger includes diethylaminoethyl (DEAE) type and quaternary aminoethyl (QAE) type. DEAE type includes DEAE-Agarose (product name: DEAE-Sepharose, Amersham), DEAE-Dextran (product name: DEAE-Sephadex, Amersham), DEAE-Polyvinyl (product name: DEAE-TOYOPEARL, Tosoh Corporation) and the like. QAE type includes QAE-Agarose (product name: QAE-Sepharose, Amersham), QAE-polyvinyl (product name: QAE-TOYOPEARL, Tosoh Corporation) and the like. In this process, any carrier material may be used but, as for the functional groups, a weak anion exchanger may preferably be used. Any type of a buffer may be used for the anion exchange process but pH of the buffer when a modified major mite allergen is contacted with the column may be in a range of 7 to 10, preferably of pH 8 to 9. A salt concentration may be used in a range of 0.03 to 0.1M, preferably 30 to 60 mM. This purification process removes most of contaminating proteins.

(v) Recovery of Adsorbed Fractions with Treatment with Hydrophobic Chromatographic Gel The non-adsorbed fractions obtained by treatment with the anion exchanger as described above are contacted with a hydrophobic column, in which a buffer is exchanged with a buffer containing sodium chloride and the column is equilibrated with said buffer, to let a modified major mite allergen adsorbed to the column. A concentration of sodium chloride may be in a range of 2 to 3 M, preferably 3 M. A buffer as used herein may be any type of a buffer at a concentration of 5 to 50 mM, preferably 10 to 20 mM, at pH of 7 to 8. An example of a hydrophobic gel includes a phenyl type, a butyl type, an octyl type, and the like. A carrier material includes Agarose (Amersham), Dextran (Amersham), Polyvinyl (Tosoh Corporation), and the like. In this purification process, any carrier material may be used but, as for the functional groups, a butyl type may preferably be used.

Then, after thoroughly washing the column with the same buffer as used for equilibrium, a modified major mite allergen is eluted from the hydrophobic column by decreasing a salt concentration. A salt concentration may be decreased by any means such as using a concentration gradient or decreasing a salt concentration stepwise. In addition to sodium chloride, a chemical substance used for changing a salt concentration includes ammonium sulfate, ammonium acetate, ammonium chloride, ammonium nitrate, potassium acetate, potassium chloride, sodium acetate, calcium chloride, magnesium chloride, etc., any of which may be used. In accordance with the present invention, stepwise procedure may preferably be used. A salt concentration while elution is 0 to 1 M, preferably 0 M. A series of column procedures of hydrophobic chromatographic treatment may preferably be performed at 5 to 10° C.

(vi) Recovery of Adsorbed Fractions with Treatment with Anion Exchanger

The non-adsorbed fractions obtained by treatment with the hydrophobic column as described above are contacted with an anion exchanger column, in which a buffer is exchanged with a buffer containing urea and the column is equilibrated with said buffer, to let a modified major mite allergen adsorbed to the column. Urea contained in the buffer inhibits coagulation of a modified major mite allergen. A concentration of urea may be in a range of 0.5 to 5 M, preferably 1 to 3 M. A buffer as used herein may be any type of a buffer at a concentration of 5 to 50 mM, preferably 10 to 20 mM, at pH of 8 to 10, preferably 8.5 to 9.5. In this purification process as well, any carrier material may be used but, as for the functional groups, a strong anion exchanger may preferably be used.

Then, after thoroughly washing the column with the same buffer as used for equilibrium, a modified major mite allergen is eluted from the anion, exchanger column by increasing a salt concentration. A salt concentration may be increased by any means such as using a concentration gradient or increasing a salt concentration stepwise. A chemical substance used for changing a salt concentration may include sodium chloride, potassium chloride, calcium chloride, magnesium chloride, etc., any of which may be used. In accordance with the present invention, a concentration gradient may be used. A concentration gradient may be prepared by dissolving sodium chloride in the same buffer as used for equilibrium of the column. A salt concentration while elution is 0 to 0.5 M, preferably 0 to 0.1 M. A series of column procedures of treatment with an anion exchanger may be performed at 5 to 10° C. The obtained solution containing a modified major mite allergen, after being dialyzed to PBS and aseptically filtered through a filter of ϕ0.22 μm, is stored for use as a modified major mite allergen.

Analysis of a Modified Major Mite Allergen

Property of a modified major mite allergen at each purification step or after completion of all the purification steps may be elucidated by the techniques routinely used for protein analysis including, for instance, EIA and Western blot with a specific antibody, SDS-polyacrylamide gel electrophoresis (SDS-PAGE) under reductive and non-reductive conditions, high performance liquid chromatography (HPLC), endotoxin test, measurement of absorbance, isoelectric focusing, and the like.

A purified modified major mite allergen obtained by the process for purification in accordance with the present invention, in case that a modified major mite allergen obtained by the genetic recombination technique is a modified major mite allergen Der f 2 wherein both the cysteine residues at 8-position and 119-position in Der f 2 are replaced with serine residues, has a molecular weight of about 15 kD and isoelectric point of pI 6.6 to 7.2 and is obtained as a recombinant protein of high purity characterized by the following properties: (1) a single band in SDS-PAGE analysis; (2) a content of contaminating proteins from a host that is 0.1% or less; (3) a content of a polymer of the modified major mite allergen that is less than a detection limit; (4) a content of the modified major mite allergen with distinct steric structure that is 10% or less; and (5) an endotoxin content of a solution containing 500 μg/ml of the modified major mite allergen that is less than 0.25 EU/ml, a quality standard for water for injection (Japanese Pharmacopoeia, 14th edition).

Formulation

The obtained purified modified major mite allergen may be formulated into pharmaceutical preparations by addition of commonly used additives such as e.g. a stabilizing agent, a surfactant, or a buffer, aseptic filtration, filling, lyophilization, and the like. The thus formulated preparations containing a modified major mite allergen, like a mite allergen extract or a house dust extract, may be used as clinical preparations for therapy of allergic diseases in the form of injections or dosage forms for transmucous administration (intranasal, oral, sublingual).

The present invention is explained in more detail by means of the following Examples.

In the following Examples, a modified major mite allergen obtained by the genetic recombination technique is purified for a modified major mite allergen Der f 2 wherein both the cysteine residues at 8-position and 119-position in Der f 2 are replaced with serine residues but the present invention should not be construed to be limited thereto.

EXAMPLE 1

Preparation of Recombinant *E. coli* Producing Modified Major Mite Allergen

First, a gene fragment was constructed in which a gene fragment (C8/119S) of a modified major mite allergen (a modified major mite allergen Der f 2 wherein both the cysteine residues at 8-position and 119-position in Der f 2 are replaced with serine residues) was bound downstream of Trp promoter as described below.

A gene fragment containing Trp promoter was prepared according to the method reported by Ikehara et al. (Proc. Natl. Acad. Sci. USA, Vol. 81, pp. 5956-5960, 1984). To the 5' and 3' ends of the resulting tryptophan promoter gene fragment were bound EcoRI linkers (TaKaRa) and the obtained gene fragment was inserted at the EcoRI site of pBR322 to prepare a recombinant vector pW.

Next, a nucleic acid fragment containing a modified major mite allergen gene (C8/119S) was obtained by PCR using as a template a plasmid pFLT11-C8/119S (Japanese Patent Publication No. 253851/1994) bearing said modified major mite allergen gene, a synthetic primer containing at its 5' end restriction enzyme site NspV (SEQ ID NO: 1) and a synthetic primer containing at its 3' end restriction enzyme site NruI (SEQ ID NO: 2).

A fragment obtained by complete digestion of this nucleic acid fragment with restriction enzymes NspV and NruI was linked with the recombinant vector pW completely digested with restriction enzymes ClaI and NruI with T4 ligase (TaKaRa) to prepare an expression vector pW11-C8/119S.

Next, for increasing an expression level, replication origin from pBR322 contained in pW11-C8/119S was replaced with that from pUC18. Plasmid pUC18 was completely digested with restriction enzymes PvuI and PvuII to obtain a gene fragment containing a desired replication origin. On the other hand, the plasmid pW11-C8/119S was completely digested with NdeI and, after filling the cohesive ends, completely digested with PvuI to obtain a nucleic acid fragment containing the modified major mite allergen gene (C8/119S). The thus prepared two nucleic acid fragments were linked together with T4 ligase to prepare an expression plasmid pWU11-C8/119S (FIG. 1).

*E. coli* strain HB101 was transformed with the obtained expression plasmid pWU11-C8/119S to obtain recombinant *E. coli* strain pWU11-C8/119S/HB101, which was used as a strain for producing the desired modified major mite allergen and stocked in glycerol.

EXAMPLE 2

Purification of Modified Major Mite Allergen (1) Pretreatment of Culture (Recovery of Inclusion Bodies)

Figure 2:
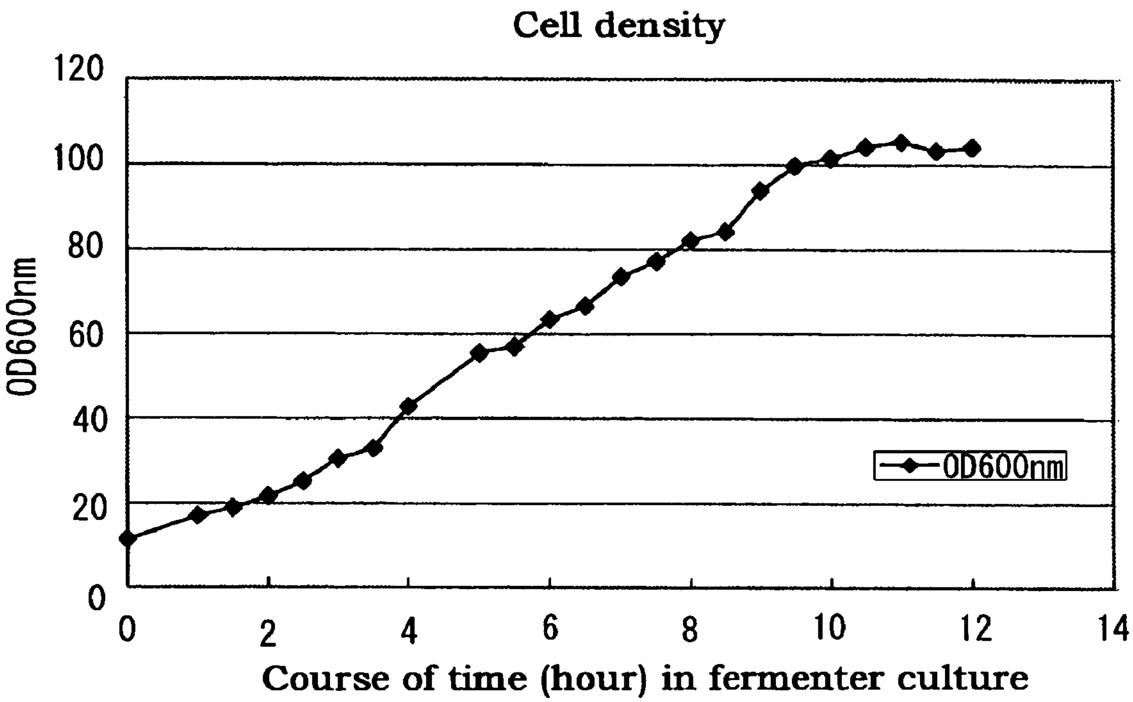
FIG. 2 shows a growth curve of cells while fermenter culture.
Figure 3:
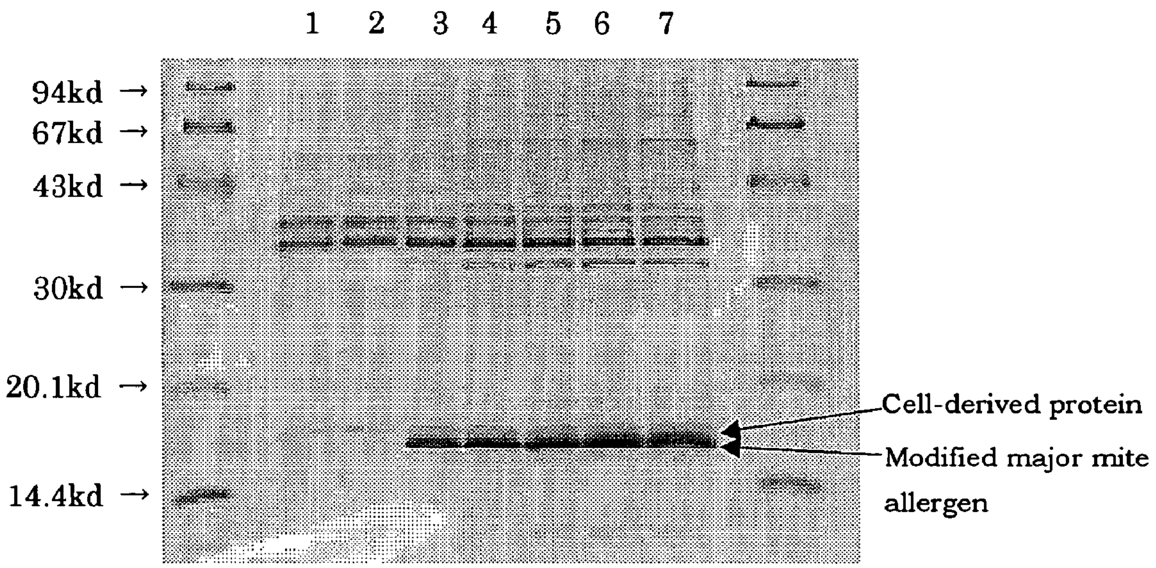
FIG. 3 shows results of SDS-polyacrylamide gel electrophoresis of a sonicate of recombinant *E. coli* cells proliferated in a fermenter culture, a sampling of which was performed with passage of time, in which Lane 1: before shifting to 37° C.; Lane 2: 1 hour after the temperature shifting to 37° C.; Lane 3: 3 hours after the temperature shifting; Lane 4: 5 hours after the temperature shifting; Lane 5: 7 hours after the temperature shifting; Lane 6: 9 hours after the temperature shifting; and Lane 7: 12 hours after the temperature shifting.

Ten milliliters of the glycerol stock of the strain producing the desired modified major mite allergen were inoculated to 1.5 L of LB medium and shake-cultured at 35° C. for 8 hours to prepare a cell suspension. The cell suspension was inoculated to 250 L of LB medium for aeration culture at 25° C. overnight. Then, the culture temperature was raised to 37° C. and aeration culture was further continued for 8 to 12 hours, while adding an amino acid and glucose depending on proliferation of the cells, to allow for production of a modified major mite allergen within the cells as inclusion bodies (FIGS. 2 and 3).

The culture (about 300 L) was concentrated to about 100 L using MF membrane (Microza; ASAHIKASEI) to recover the *E. coli* cells. The recovered *E. coli* cells were diluted 4-fold with deionized water and then concentrated to about 100 L with the MF membrane. The procedure of dilution with deionized water and concentration with the MF membrane was repeated three times in total to remove any contaminating culture components. The *E. coli* cells were further diluted once with 20 mM Tris buffer at pH 8.5 followed by concentration and buffer exchange. To the resulting cells was added lysozyme at a final concentration of 0.6 g/L. After stirring for 30 minutes, the mixture was transferred to a low-temperature workroom (10° C. or less) and was left to stand overnight to let the cell wall of the cells lysed. The lysozyme solution was subject to French Press (GAULIN CORPORATION) until vanishing of viscosity to disrupt the cells. Due to exothermal reaction when the cells are disrupted, the solution was cooled to 18° C. or less with a heat exchanger. The solution of cell disruption was then subject to three repetitions of the procedures of dilution with deionized water to 400 L and concentration with MF membrane to 100 L so as to remove the cellular components. The concentrated solution of inclusion bodies was centrifuged at 3,000 rpm for 3 hours to precipitate and recover inclusion bodies. The recovered inclusion bodies were measured to weigh 2.5 kg as a wet weight.

(2) Refolding Treatment

About 100 g of the inclusion bodies was put in 10 L of 20 mM Tris buffer at pH 8.5 containing 8 M urea and 10 mM cysteine and the mixture was stirred at room temperature for 30 minutes to dissolve. The solution was diluted into 150 L of Tris buffer at pH 8.5 containing 3 mM cysteine and 0.3 mM cystine. The diluted solution was transferred to a low-temperature workroom and left to stand for 4 days for refolding reaction.

(3) Ultrafiltration

The refolding reaction was quenched by titration of the above solution to pH 7 with 30% acetic acid. The solution was concentrated to about 10 L with ultrafiltration membrane of fractionation M. W. of 10,000 (Sartorius). To the resultant concentrate was added sodium chloride at a final concentration of 50 mM. The mixture was adjusted to pH 8.5 by titration with a 5N aqueous solution of sodium hydroxide. Insoluble material was removed from the mixture with a filter of ϕ0.45 μm (Sartorius).

(4) Weak Anion Exchange Chromatography

A column of ϕ14 cm (Amicon) was charged with 2 L of DEAE-TOYOPEARL 650M (Tosoh Corporation) and equilibrated with 20 mM Tris buffer at pH 8.5 containing 50 mM sodium chloride. The refolding solution was passed through the column and about 10 L of effluent fractions were recovered. A flow rate was set at 60 cm/h or less. This procedure could remove most of contaminating proteins. The recovered effluent fractions were, after buffer exchange with 20 mM phosphate buffer at pH 7.2 containing 3 M sodium chloride, were filtered through a filter of ϕ0.45 μm.

(5) Hydrophobic Chromatography

A column of φ14 cm (Amicon) was charged with 2 L of Butyl-Sepharose FF (Pharmacia) and equilibrated with 20 mM phosphate buffer at pH 7.2 containing 3 M sodium chloride. Then, the above filtrate solution was passed through the column to let a modified major mite allergen adsorbed to the column. After thoroughly washing the column with the same buffer as used for equilibrium, the modified major mite allergen was eluted with 20 mM phosphate buffer at pH 7.2 to recover about 2 L of effluent fractions. A flow rate was set at 60 cm/h or less. The recovered effluent fractions, after buffer exchange with 20 mM Tris buffer at pH 8.5 containing 2 M urea, were filtered through a filter of φ0.22 μm.

(6) Strong Anion Exchange Chromatography

A column of φ14 cm (Amicon) was charged with 1 L of QAE-TOYOPEARL 550C (Tosoh Corporation) and equilibrated with 20 mM Tris buffer at pH 8.5 containing 2 M urea. Then, the above filtrate solution was passed through the column to let a modified major mite allergen adsorbed to the column. After thoroughly washing the column with the same buffer as used for equilibrium, the modified major mite allergen was eluted with a linear gradient of sodium chloride from 0 to 100 mM (20 column volumes) to recover about 3 L of effluent fractions. A flow rate was set at 60 cm/h or less.

The effluent fractions containing the modified major mite allergen were dialyzed to 10 mM phosphate buffer (PBS) at pH 7.2 containing 140 mM sodium chloride and aseptically filtered through a filter of φ0.22 μm (Millipore) to obtain a solution of a purified modified major mite allergen (about 4 L, about 500 μg/ml; Lot Nos.: SF-01, FP-020 and FP-021).

EXAMPLE 3

Analysis of Modified Major Mite Allergen (1) Western Blot Analysis

Figure 4:
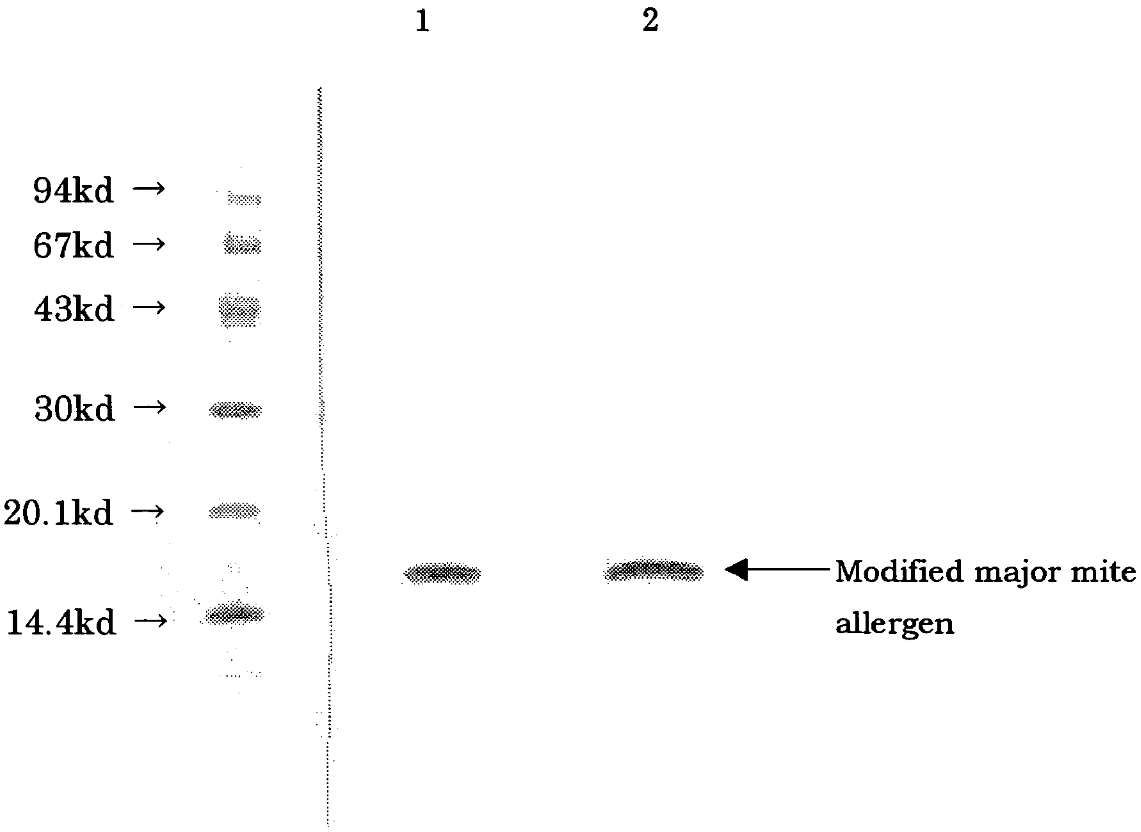
FIG. 4 shows results of Western blot analysis using anti-Der f 2 monoclonal antibody in which Lane 1: non-reductive treatment of a purified modified major mite allergen; and Lane 2: reductive treatment of a purified modified major mite allergen.

A modified major mite allergen was detected with Western blotting. Samples were diluted to an appropriate concentration with water for injection and, under non-reductive condition and after reduction with 2-mercaptoethanol, added to SDS-polyacrylamide gel (Funakoshi Co., Ltd.) for electrophoresis. The electrophoretic gel was immersed in a Trans electrophoresis buffer (10 mM CAPS containing 10% methanol) for 5 minutes and then the proteins in the gel were transferred to PVDF membrane with Trans Western electrophoresis transfer devise. After transfer, the PVDF membrane was immersed in 10 mM Tris buffer containing 2% bovine serum albumin, 0.1% Tween 20 and 0.5 M sodium chloride for blocking at 37° C. for 2 hours. Then, 5 μg/ml of anti-Der f 2 monoclonal antibody was added to the PVDF membrane for reaction at 37° C. for 2 hours. After washing the PVDF membrane five times in total with 10 mM Tris buffer containing 0.1% Tween 20 and 0.5 M sodium chloride (hereinafter referred to as "TNT buffer"), a solution of anti-mouse IgG antibody labeled with HRP diluted to 20,000-fold was added to the membrane for reaction at 37° C. for 2 hours. After washing the PVDF membrane five times in total with TNT buffer, a 0.05% DAB solution was added to the membrane for development to detect the modified major mite allergen (FIG. 4).

(2) ELISA Analysis (i) Determination of Amount of Modified Major Mite Allergen Contained in Sample at each Purification Step To each well of ELISA plate (Nunc) were added each 100 μl of mouse anti-Der f 2 monoclonal antibody (5 μg/ml) and the plate was coated at 4° C. overnight. After washing the plate three times in total with PBS containing 0.05% Tween 20 (hereinafter referred to as "PBST"), each 200 μl of PBS containing 1% bovine serum albumin were added to the plate for blocking at 37° C. for 1 hour. After washing the plate three times in total with PBST, the plate was added with each 100 μl of a standard solution and sample solutions as appropriately diluted and was left to stand at 37° C. for 2 hours. After washing the plate three times in total with PBST, the plate was added with each 100 μl of a rabbit anti-C8/119S polyclonal antibody diluted to 2,000-fold and was left to stand at 37° C. for 1 hour. After washing the plate three times in total with PBST, the plate was added with each 100 μl of a donkey anti-rabbit IgG antibody labeled with horseradish peroxidase and was left to stand at 37° C. for 1 hour. After washing the plate three times in total with PBST, the plate was added with each 100 μl of TMB solution (Sigma) for reaction for 30 minutes with shielding of light. The reaction was quenched by adding each 100 μl of 1N sulfuric acid and absorbance at 450 nm was measured to calculate an amount of the modified major mite allergen. The results are shown in Table 1.

TABLE 1

| Purification step | Conc. (μg/ml) | Volume (L) | Amount of protein (g) |
|---|---|---|---|
| Refolding treatment | 90 | 160 | 14.4 |
| Weak anion exchange chromatography | 700 | 10 | 7.0 |
| Hydrophobic chromatography | 4,000 | 1.5 | 6.0 |
| Strong anion exchange chromatography | 750 | 3.0 | 2.3 |

(ii) Measurement of Content of Host-Derived Contaminating Components Contained in Modified Major Mite Allergen ELISA plate (Nunc) was coated with 10 μg/ml of guinea pig anti-host-derived contaminating component polyclonal antibody at 4° C. overnight. After washing the plate three times in total with PBS containing 0.05% Tween 20 (PBST), each 200 μl of Block Ace (Dainippon Shiyaku) were added to the plate for blocking at 37° C. for 1 hour. After washing the plate three times in total with PBST, the plate was added with each 100 μl of sample solutions of modified major mite allergen from the final purification step and was left to stand at 37° C. for 2 hours. After washing the plate three times in total with PBST, the plate was added with each 100 μl of a rabbit anti-host-derived contaminating component polyclonal antibody (1 μg/ml) and was left to stand at 37° C. for 1 hour. After washing the plate three times in total with PBST, the plate was added with each 100 μl of a donkey anti-rabbit IgG antibody labeled with horseradish peroxidase and was left to stand at 37° C. for 1 hour. After washing the plate three times in total with PBST, the plate was added with each 100 μl of TMB solution (Sigma) for reaction for 10 minutes with shielding of light. The reaction was quenched by adding each 100 μl of 0.3N sulfuric acid and absorbance at 450 nm was measured to calculate an amount of the host-derived contaminating component. A content of the host-derived contaminating component is shown in Table 2. A detection limit in this ELISA system was 0.004%.

TABLE 2

| Lot Nos. | Content of host-derived contaminating component |
|---|---|
| FP-020 | 0.098% |
| FP-021 | 0.088% |

(3) SDS-PAGE Analysis

Figure 5:
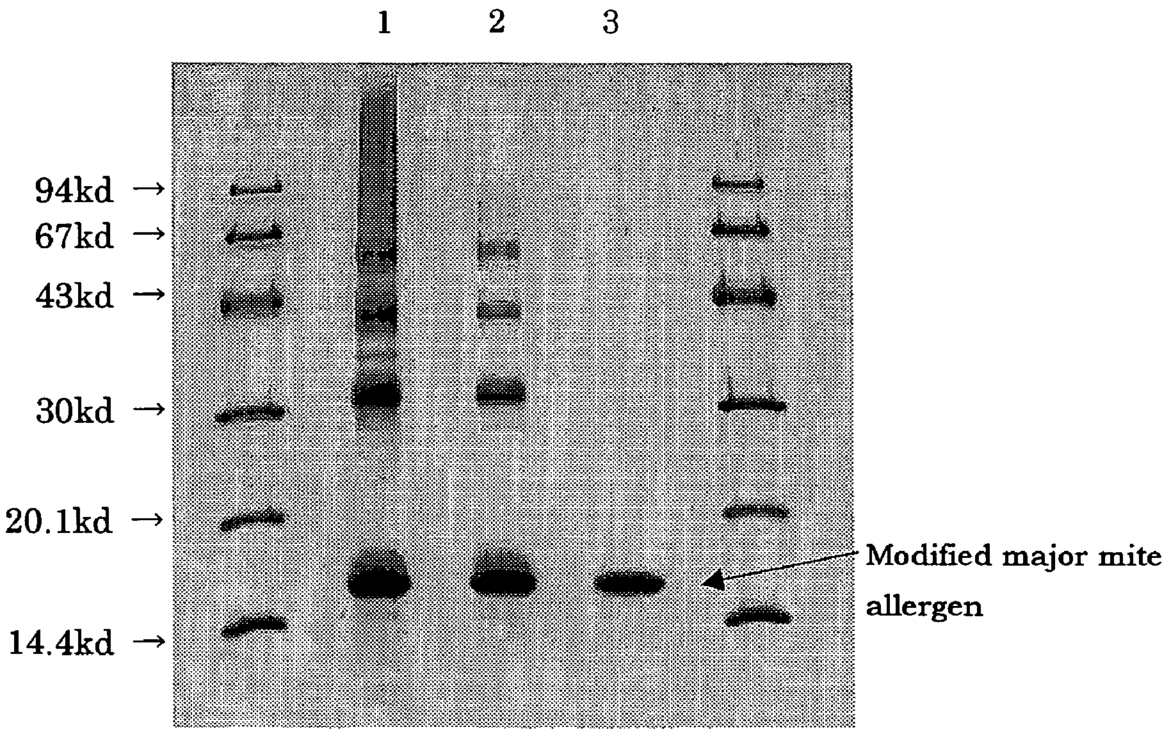
FIG. 5 shows results of SDS-polyacrylamide gel electrophoresis of a modified major mite allergen at each purification step in which Lane 1: refolding; Lane 2: weak anion exchange chromatography; and Lane 3: purified modified major mite allergen.

The contaminating proteins contained in the modified major mite allergen were analyzed by reducing the samples from each purification step with 2-mercaptoethanol, electrophoresing an amount equivalent to 2 μg of the modified major mite allergen on polyacrylamide gel (Funakoshi Co., Ltd.), and developing with Coomassie Brilliant Blue. The conditions of electrophoresis were as described in the instructions attached to the device. It could be confirmed that the more the purification steps advanced the less bands of contaminating proteins appeared (FIG. 5).

Figure 6:
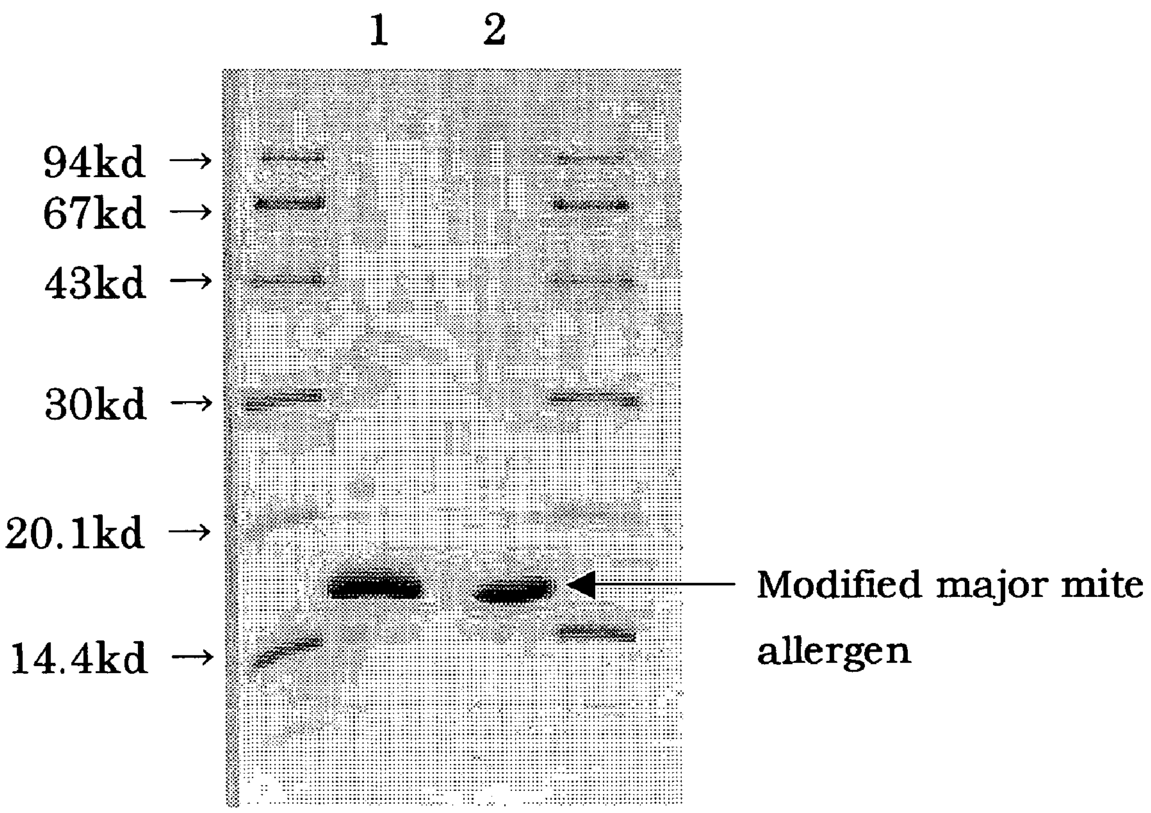
FIG. 6 shows results of SDS-polyacrylamide gel electrophoresis of a purified modified major mite allergen in which Lane 1: non-reductive treatment of a purified modified major mite allergen; and Lane 2: reductive treatment of a purified modified major mite allergen.

The samples from the final purification step were, after non-reductive or reductive treatment, subject to SDS-PAGE under the same conditions as described above. As a result, the modified major mite allergen was confirmed to be present in a band of M.W. of about 15 kD (FIG. 6).

(4) HPLC Analysis

Purity of the modified major mite allergen from the final purification step was measured by HPLC. A content of a polymer of the modified major mite allergen was measured by a gel filtration chromatography and a content of the modified major mite allergen with distinct steric structure due to wrong S—S bond formation etc. was measured by a reversed phase chromatography.

(i) Gel Filtration Chromatography

Figure 7:
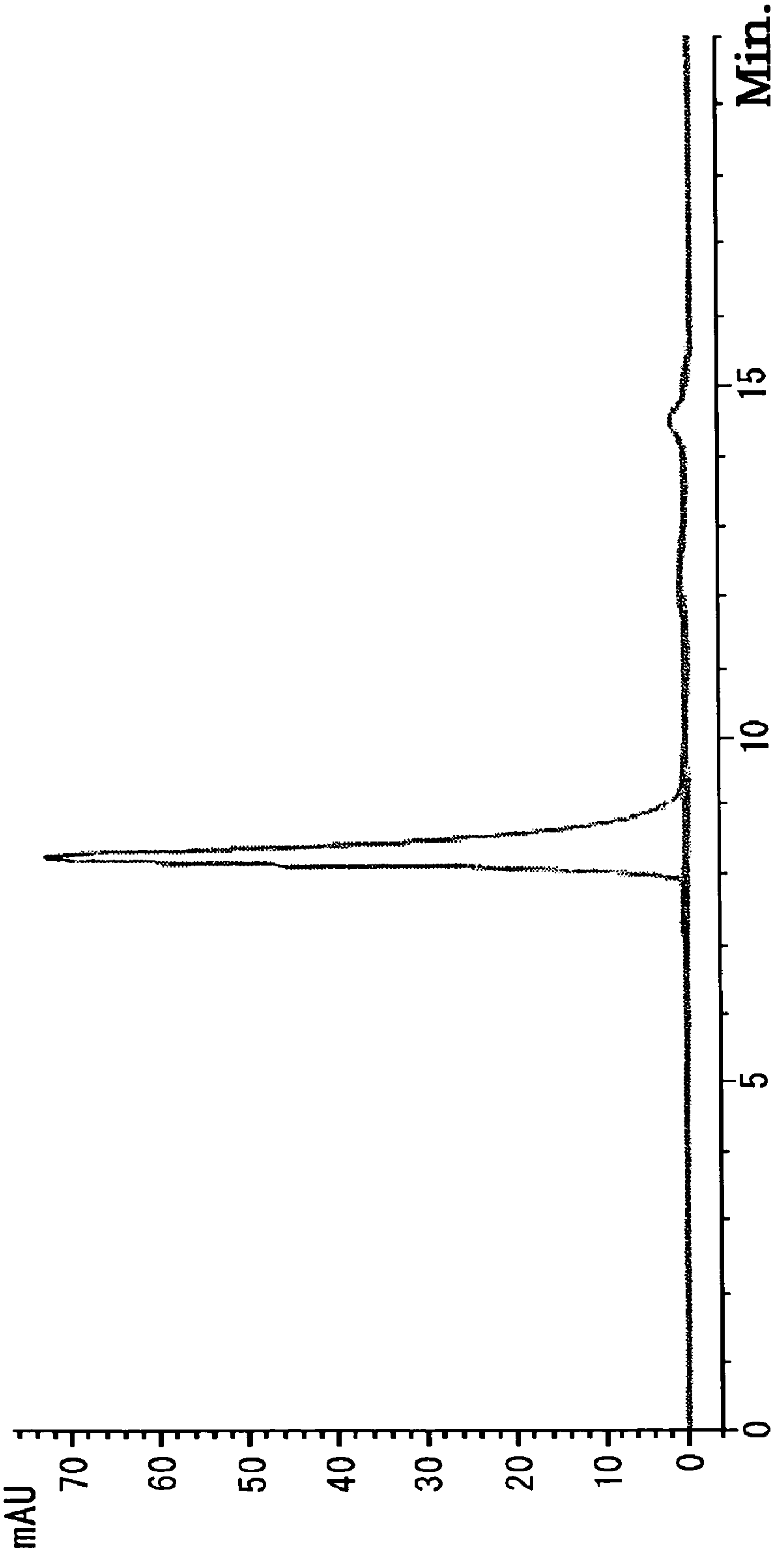
FIG. 7 shows a chromatographic pattern obtained by gel filtration HPLC analysis of a purified modified major mite allergen.

An analytic column used was G3000SW$_{XL}$ (Tosoh Corporation). A 60% acetonitrile solution containing 0.1% TFA was used as a mobile phase. A flow rate was 1 ml/min. and analytical time was set for 20 minutes. Each 100 μl of samples containing about 500 μg/ml of the modified major mite allergen were used for analysis. Twelve minutes after initiation of the analysis, solvent-derived peaks began to be detected. Therefore, analysis was within 12 minutes and a relative content of a polymer of the modified major mite allergen was calculated from an integral for 12 minutes. A content of a polymer of the modified major mite allergen was found to be less than a detection limit (FIG. 7). A detection limit of the gel filtration chromatography was 0.005%.

(ii) Reversed Phase Chromatography

Figure 8:
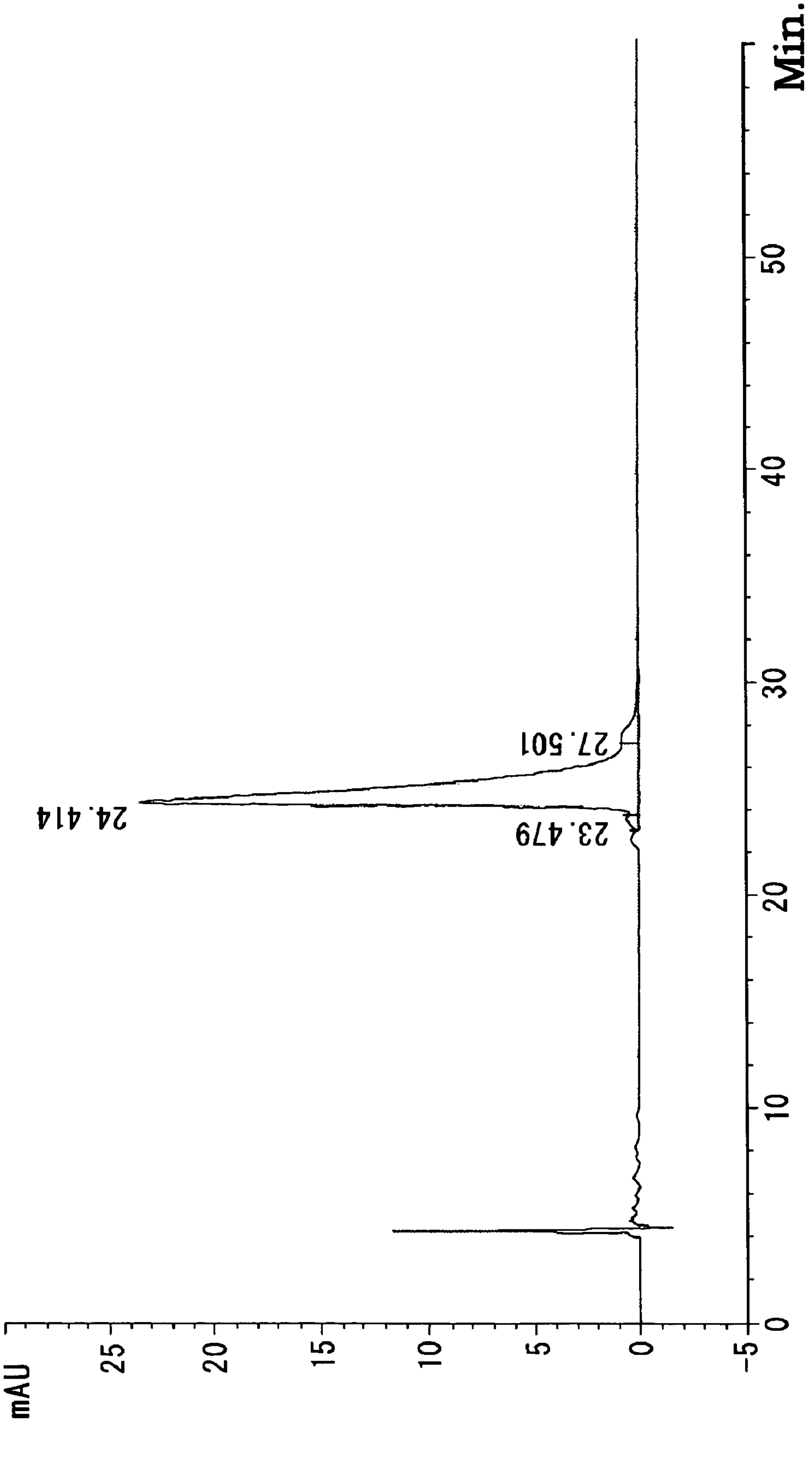
FIG. 8 shows a chromatographic pattern obtained by reversed phase HPLC analysis of a purified modified major mite allergen.

An analytic column used was CAPCELL PAK C1 (Shiseido Company, Limited). As a mobile phase, 0.1% TFA for A buffer and a 70% acetonitrile solution containing 0.1% TFA for B buffer were used. For analytical conditions, a flow rate was 1 ml/min. and a linear gradient of a mixed ratio of B buffer from 28.6% to 50% in 60 minutes was used. Each 100 μl of samples containing about 500 μg/ml of the modified major mite allergen were used for analysis. Immediate after initiation of the analysis, noise was detected. Therefore, analysis was from 13 minutes up till 60 minutes and a relative content of a major peak was calculated from an integral during this period. A relative content of the modified major mite allergen of interest was found to be 90% or more, in other words, a content of the modified major mite allergen with distinct steric structure was 10% or less (FIG. 8). A detection limit of the reversed phase chromatography was 0.03%.

(5) Endotoxin Test

An endotoxin content of the modified major mite allergen from the final purification step was measured. A reagent kit manufactured by SEIKAGAKU CORPORATION was used and a measurement was made as described in the instructions attached to the reagent. The results are shown in Table 3. An endotoxin content of a solution of the modified major mite allergen (500 μg/ml) was less than 0.25 EU/ml, a quality standard for water for injection (Japanese Pharmacopoeia, 14th edition). A detection limit of the endotoxin text was 0.002 EU/ml.

TABLE 3

Measurement of endotoxin

| Lot Nos. | Endotoxin content |
|---|---|
| FP-020 | 0.0100 EU/ml |
| FP-021 | 0.0028 EU/ml |

(6) Isoelectric Focusing

Figure 9:
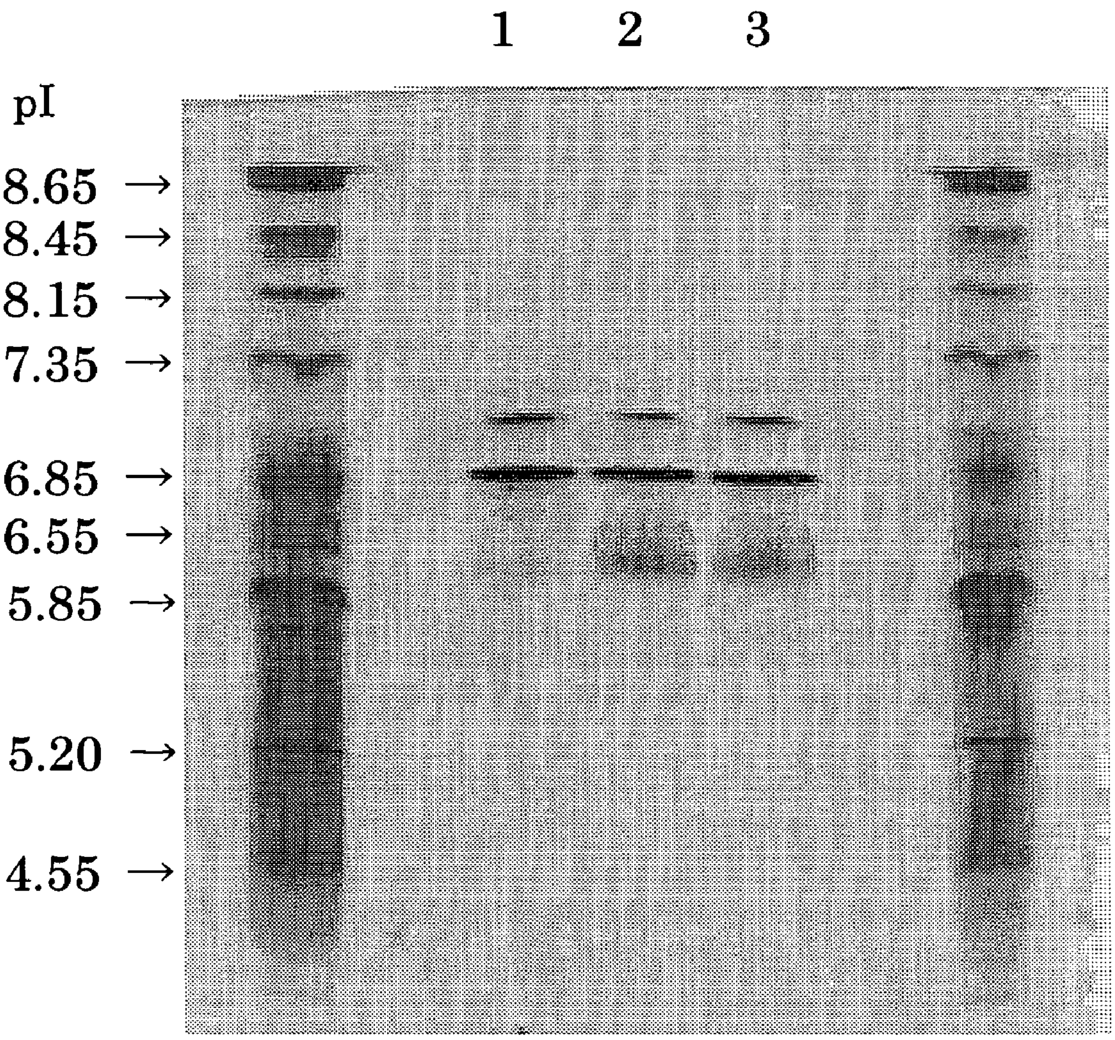
FIG. 9 shows results of isoelectric focusing of purified modified major mite allergens (3 lots) in which Lane 1: SF-01; Lane 2: FP-020; and Lane 3: FP-021.

The modified major mite allergen from the final purification step (Lot Nos.: SF-01, FP-020, FP-021) was diluted with water for injection to 150 μg/ml and was subject to isoelectric focusing with First System (Pharmacia). Isoelectric focusing was performed as described in the instruction manual attached to the device and the gel after electrophoresis was stained with silver. As a result, it was estimated that the purified modified major mite allergen had an isoelectric point of pI 6.6 to 7.2 (FIG. 9).

(7) Analysis of Polyacrylamide Gel Electrophoresis

Figure 10:
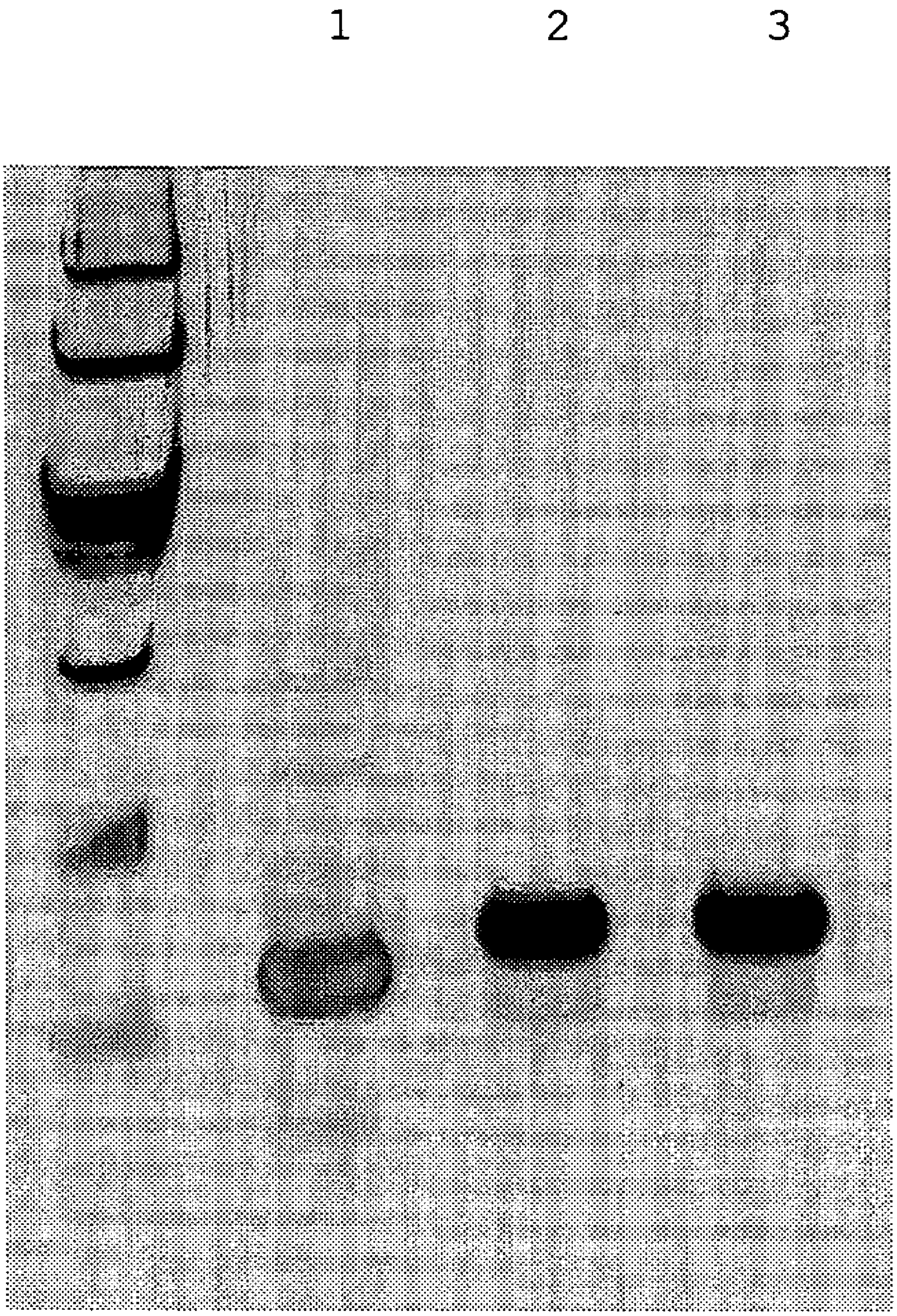
FIG. 10 shows results of SDS-polyacrylamide gel electrophoresis of the conventional purified Der f 2 (Asahi Beer Pharmaceuticals) and the purified modified major mite allergen of the present invention in which Lane 1: Der f 2; Lane 2: a modified major mite allergen FP-020; and Lane 3: a modified major mite allergen FP-021.

The modified major mite allergen from the final purification step (Lot Nos.: FP-020, FP-021) and the conventional purified Der f 2 (Asahi Beer Pharmaceuticals) were diluted with a saline to 200 μg/ml and was subject to SDS-polyacrylamide gel electrophoresis by adding each 1 μg per lane. The electrophoresed gel was stained with a silver stain kit (Daiichi Pure Chemicals Co., Ltd.) (FIG. 10).

The invention claimed is:

1. A method for purifying a major mite allergen from Der f 2 obtained by the genetic recombination technique, which comprises the following purification steps (a) to (f):

(a) Washing and recovering *Escherichia coli* cells producing the major mite allergen Der f 2 from culture using MF membrane, disrupting *E. coli* cells to release their inclusion bodies, washing the inclusion bodies using MF membrane and recovering the inclusion bodies by centrifugation;

(b) Dissolving the inclusion bodies using a reducing agent and a denaturing agent, wherein said reducing agent is selected from the group consisting of cysteine, glutathione, dithiothreitol and 2-mercaptoethanol and said denaturing agent is selected from the group consisting of urea and guanidine hydrochloride, and diluting the dissolved inclusion bodies in 10 to 20-fold amount of redox buffer comprising cysteine and cystine;

(c) Ultrafiltering the solution using an ultrafiltration membrane of fractionation M.W. of 6,000 to 10,000 to remove low molecular weight components;

(d) Passing the solution through a weak anion exchanger column equilibrated with a buffer of pH 7 to 10 and a salt concentration of 0.03 to 0.1M and collecting the non-adsorbed effluent;

(e) Contacting the effluent with a hydrophobic column equilibrated with a 2 to 3M sodium chloride buffer of pH 7 to 8, washing the column, and eluting the major mite allergen Der f 2 by decreasing the sodium chloride concentration of the buffer; and (f) Contacting the eluted major mite allergen Der f 2 with a strong anion exchanger column by equilibrating at pH 8.5 to 9.5 and at 1 to 3M urea and then eluting the adsorbed major mite allergen Der f 2 by increasing the salt concentration and dialyzing the major mite allergen Der f 2 with PBS followed by aseptic filtration.

2. The method for purification according to claim 1, wherein the major mite allergen Der f 2 obtained by the genetic recombination technique is a modified major mite allergen Der f 2 wherein both the cysteine residues at 8-position and 119-position in Der f 2 are replaced with serine residues.

* * * * *

UNITED STATES PATENT AND TRADEMARK OFFICE

CERTIFICATE OF CORRECTION

PATENT NO. : 7,667,009 B2
APPLICATION NO. : 10/555883
DATED : February 23, 2010
INVENTOR(S) : Koyanagi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 812 days.

Signed and Sealed this

Seventh Day of December, 2010

David J. Kappos
*Director of the United States Patent and Trademark Office*